United States Patent [19]

Nakai et al.

[11] Patent Number: 5,075,437
[45] Date of Patent: Dec. 24, 1991

[54] 3,4-DISUBSTITUTED-2-AZETIDINONE DERIVATIVES AND PROCESSES FOR PREPARATION USING TIN ENOLATES

[75] Inventors: Takeshi Nakai, Yokohama; Fumiyuki Shirai, Ikeda; Toshiyuki Chiba, Osaka; Hiroaki Ohtake, Suita, all of Japan

[73] Assignee: Fujisawa Pharmaceutical Co., Ltd., Osaka, Japan

[21] Appl. No.: 518,993

[22] Filed: May 4, 1990

Related U.S. Application Data

[60] Division of Ser. No. 141,420, Jan. 7, 1988, abandoned, which is a continuation-in-part of Ser. No. 31,129, Mar. 30, 1987, abandoned.

[30] Foreign Application Priority Data

Apr. 1, 1986 [GB] United Kingdom ............... 8607921

[51] Int. Cl.$^5$ ................. C07B 37/04; C07D 205/08
[52] U.S. Cl. .................................................. 540/200
[58] Field of Search ........................................ 540/200

[56] References Cited

PUBLICATIONS

Nomenclature of Organic Chemistry, 1979 Edition (International Union of Pure and Applied Chemistry), Pergamon Press 1979, pp. 75, 76, 257, 258.
Iwasawa, Chem. Letters, p. 1045 (1985).
Iwasawa, Chem. Letters p. 297 (1983).
Mukaiyama, Tet. Letters, 40, 1381 (1984).
Nagao, J. Chem. Soc. Chem. Comm. 1985, 1418.
Nagao, J. Org. Chem. 51, 2391 (1986).
Mukaiyama, Chem Abs. 101, 191759 (1984).
Mukaiyama, Chem. Abs. 98, 142907y (1982).
Shirai, J. Org. Chem. 52, 5492-4 (1987).
Nagao, J. Amer. Chem. Soc. 108, 4673 (7-31-86).
Terajima, Chem. Abs. 108, 55764f (7-14-87).
Deziel, Tet. Letters 27, 5687, (1986).
Neider, Tet. Letters 23, 379, (1982).
Neda, Con. J. Chem. 62, 2936, (1984).

Oida, Derwent for JP60-19763 Plus Translation.

*Primary Examiner*—Mark L. Berch
*Attorney, Agent, or Firm*—Oblon, Spivak, McClelland, Maier & Neustadt

[57] ABSTRACT

The invention relates to the preparation of 3,4-disubstituted-2-azetidinone compounds of the formula:

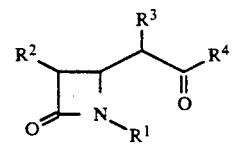

in which $R^1$ is hydrogen or amido-protective group, $R^2$ is hydroxy(lower)alkyl or protected hydroxy(lower)alkyl, $R^3$ is lower alkyl, and $R^4$ is 1-(lower)alkyl-1-hydroxy($C_2$–$C_6$)alkyl, 1-(lower)alkyl-1-(protected hydroxy)-($C_2$–$C_6$)alkyl or 2-thioxothiazolidin-3-yl, useful as an intermediate for the production of antimicrobial agents by reacting a compound a compound of the formula:

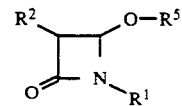

in which $R^5$ is acyl, or salts thereof, with a compound of the formula:

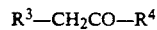

or salts thereof, in the presence of an enolizating agent selected from the group consisting of stannous(lower)alkylsulfonate and stannous perhalo(lower)alkylsulfonate.

7 Claims, No Drawings

3,4-DISUBSTITUTED-2-AZETIDINONE DERIVATIVES AND PROCESSES FOR PREPARATION USING TIN ENOLATES

This is a division of application Ser. No. 07/141,420, filed on Jan. 7, 1988, abandoned, which is a continuation-in-part of application Ser. No. 07/031,129, filed Mar. 30, 1987, now abandoned.

The present invention relates to novel 3,4-disubstituted-2-azetidinoe derivatives and salts thereof, and to processes for the preparations thereof.

More particularly, the present invention relates to novel 3,4-disubstituted-2-azetidinone derivatives and salts thereof, which are useful as intermediates for the production of antimicrobial agents, and to processes for the preparations thereof.

Accordingly, one object of the present invention is to provide novel 3,4-disubstituted-2-azetidinone derivatives and salts thereof, which are useful intermediates for the production of 1-(lower)alkylcarbapenem compounds having high antimicrobial activities against a number of pathogenic microorganisms.

Another object of the present invention is to provide processes for the preparations of 3,4-disubstituted-2-azetidinone derivatives and salts thereof.

The 3,4-disubstituted-2-azetidinone derivatives of the present invention can be represented by the following general formula:

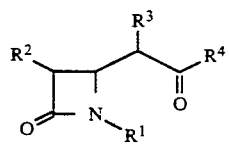

(I)

in which
R$^1$ is hydrogen or imino-protective group,
R$^2$ is hydroxy(lower) alkyl or protected hydroxy(lower)alkyl,
R$^3$ is lower alkyl, and
R$^4$ is 1-(lower)alkyl-1-hydroxy($C_2$–$C_6$)alkyl, 1-(lower)alkyl-1-(protected hydroxy)($C_2$–$C_6$)alkyl or 2-thioxothiazolidin-3-yl.

In the object compound (I) of the present invention, it is to be understood that there may be one or more stereoisomeric pair(s) such as optically active isomers due to asymmetric carbon atoms at the third and fourth positions of the 2-azetidinone ring and in the substituent of the fourth position thereof, and such isomers are also included within the scope of the present invention.

However, among the object compound (I) of the present invention, the compound represented by the following chemical formula (I') may be the most preferable and the preparation of the compound (I') proceeded in a highly stereoselective manner.

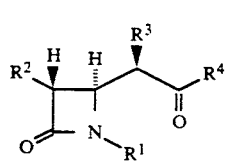

(I')

in which R$^1$, R$^2$, R$^3$ and R$^4$ are each as defined above, or salts thereof.

Accordingly, the characteristics of the present invention consist mainly in the optically active compound of the above-identified formula (I') and also in the novel process for the preparation thereof.

Suitable salts of the object compounds (I) and (I') may include conventional salts with a base such as an inorganic base salt, for example, an alkali metal salt (e.g. sodium salt, potassium salts, etc.), and the like.

According to the present invention, the object compound (I) and salts thereof can be prepared by the processes as illustrated by the following reaction schemes.

(1) Process 1:

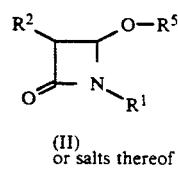 $\xrightarrow[\text{in the presence of an enolizating agent}]{R^3CH_2COR^4 \text{ (III)} \text{ or salts thereof}}$ (II)
or salts thereof

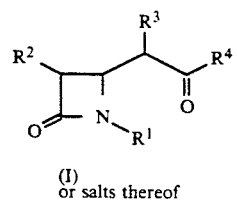

(I)
or salts thereof (2) Process 2:

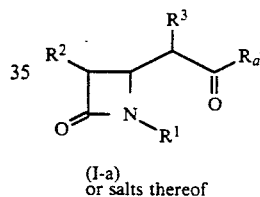 $\xrightarrow{\text{Removal of the hydroxy-protective group in } R_a^4}$ (I-a)
or salts thereof

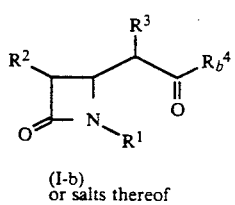

(I-b)
or salts thereof (3) Process 3:

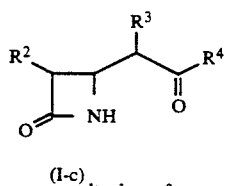 $\xrightarrow{\text{Introduction of the imino-protective group}}$ (I-c)
or salts thereof

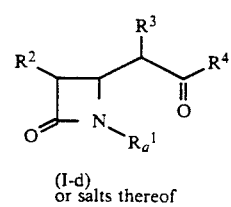

(I-d)
or salts thereof (4) Process 4:

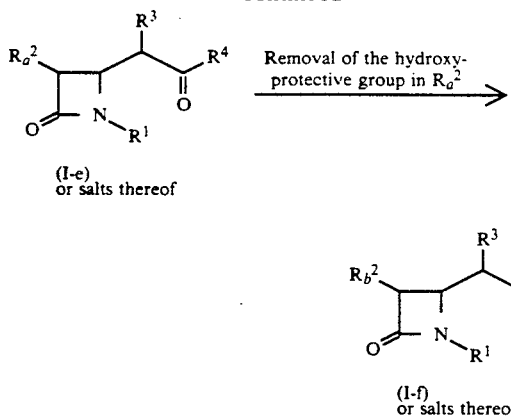

(I-e) or salts thereof

Removal of the hydroxy-protective group in $R_a^2$

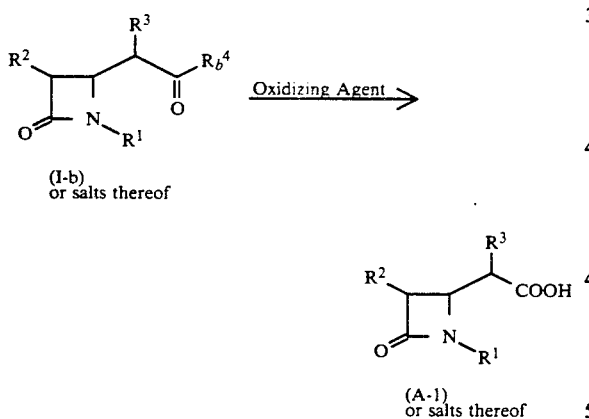

(I-f) or salts thereof in which
$R^1$, $R^2$, $R^3$ and $R^4$ are each as defined above,
$R_a^1$ is imino-protective group,
$R_a^2$ is protected hydroxy(lower)alkyl,
$R_b^2$ is hydroxy(lower)alkyl,
$R_a^4$ is 1-(lower)alkyl-1-(protected hydroxy)($C_2$-$C_6$)alkyl,
$R_b^4$ is 1-(lower)alkyl-1-hydroxy($C_2$-$C_6$)alkyl, and
$R^5$ is acyl.

The object compound (I) and salts thereof can be converted to the known key-intermediates for the production of antimicrobial 1-(lower)alkylcarbapenem compounds according to the following methods.

(A) Method A:

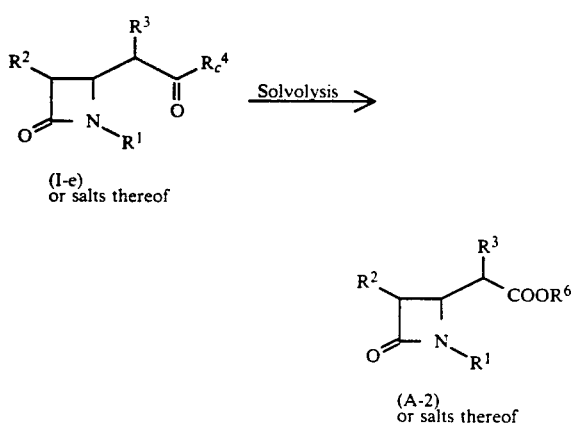

(I-b) or salts thereof

Oxidizing Agent →

(B) Method B:

(I-e) or salts thereof

Solvolysis →

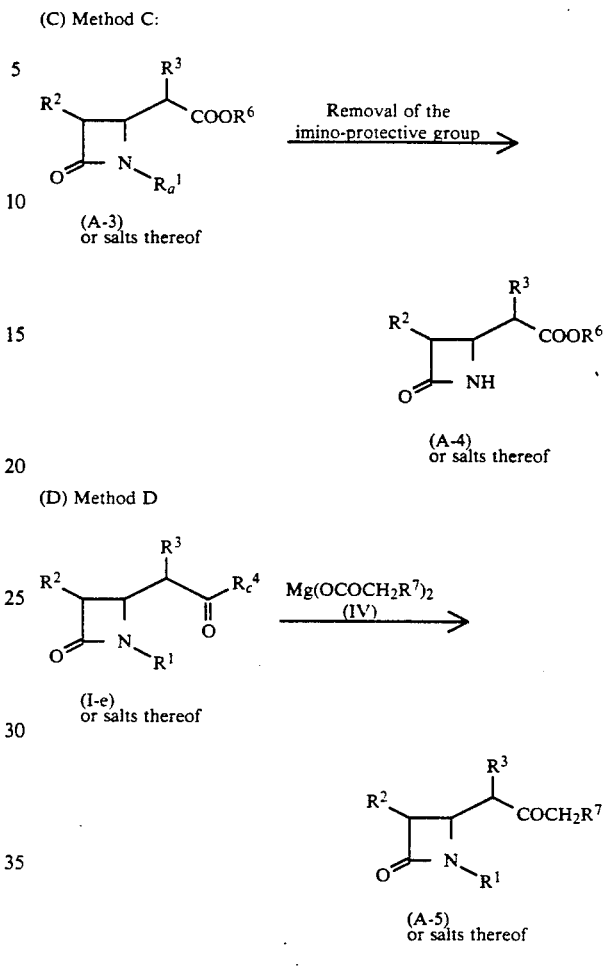

in which
$R^1$, $R_a^1$, $R^2$, $R^3$ and $R_b^4$ are each as defined above,
$R_c^4$ is 2-thioxothiazolidin-3-yl,
$R^6$ is hydrogen or lower alkyl, and
$R^7$ is protected carboxy.

In the above and subsequent descriptions of the present specification, suitable examples and illustrations of the various definitions which the present invention includes within the scope thereof are explained in detail as follows.

The term "lower" is intended to mean 1 to 6 carbon atoms, unless otherwise indicated.

Suitable "imino-protective group" (otherwise denotable as "amido-protective group") may include ar(lower)alkyl such as mono- or di- or triphenyl(lower)alkyl (e.g. benzyl, benzhydryl, trityl, etc.), acyl such as carbamoyl, aliphatic acyl, aromatic acyl, heterocylic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaroyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, tert-butoxycarbonyl, etc.), alkoxyoxalyl such as lower alkoxyoxalyl (e.g. methoxalyl, ethoxalyl, propoxyoxalyl, butoxyoxalyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cylohexanecarbonyl, etc.), and the like.

The aromatic acyl may include aroyl (e.g. benzoyl, toluoyl, xyloyl, etc.), N-arylcarbamoyl (e.g. N-phenylcarbamoyl, N-tolylcarbamoyl, N-naphthylcarbamoyl, etc.), arenesulfonyl (e.g. benzenesulfonyl, tosyl, etc.), and the like.

The heterocyclic acyl amy include heterocyclic carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include aralkanoyl such as phenyl(iower)alkanoyl (e.g. phenylacetyl, phenylpropionyl, phenylhexanoyl, etc.), aralkoxycarbonyl such as phenyl(lower)alkoxycarbonyl (e.g. benzyloxycarbonyl, phenethyloxycarbonyl, etc.), aralkoxyoxalyl such as phenyl(lower)alkoxyoxalyl (e.g. benzyloxyoxalyl, etc.), aryloxyalkanoyl such as phenoxy(lower)alkanoyl (e.g. phenoxyacetyl, phenoxypropionyl, etc.), and the like.

The aliphatic acyl substituted with heterocyclic group(s) may include heterocyclic-alkanoyl such as heterocyclic-(lower)alkanoyl (e.g. thienylacetyl, imidazolylacetyl, furylacetyl, tetrazolylacetyl, thiazolylacetyl, thiadiazolylacetyl, thienylpropionyl, thiadiazolylpropionyl, etc.), and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, and the like, and preferable acyl having such substituent(s) may be mono (or di or tri)haloalkanoyl (e.g. chloroacetyl, bromoacetyl, dichloroacetyl, trifluoroacetyl, etc.), mono (or di or tri)haloalkoxycarbonyl (e.g. chloromethoxycarbonyl, dichloromethoxycarbonyl, 2,2,2-trichloroethoxycarbonyl, etc.), nitro(or halo or lower alkoxy)aralkoxycarbonyl (e.g. nitrobenzyloxycarbonyl, chlorobenzyloxycarbonyl, methoxybenzyloxycarbonyl, etc.), nitro(or halo or lower alkoxy)aralkoxyoxalyl (e.g. nitrobenzyloxyoxalyl, etc.), mono(or di or tri)halo(lower) alkylsulfonyl (e.g. fluoromethylsulfonyl, difluoromethylsulfonyl, trifluoromethylsulfonyl, trichloromethylsulfonyl, etc.), and the like.

More preferable example of "imino-protective group" thus defined may be ar($C_1$–$C_4$)alkyl, phenyl- or nitrophenyl($C_1$–$C_4$)alkoxyoxalyl and ($C_1$–$C_4$)alkoxyoxalyl and the most preferable one may be ethoxalyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy ($C_1$–$C_4$)alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as acyl mentioned in the explanation of imino-protective group; ar(lower)alkyl, for example, mono-or di- or triphenyl(lower)alkyl (e.g. benzyl, benzhydryl, trityl, etc.), etc., trisubstituted silyl, for example, tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl, (e.g. tribenzylsilyl, etc.), etc., and the like.

More preferable example of the protected hydroxy(lower)alkyl thus defined may be tri($C_1$–$C_4$)alkylsilyloxy($C_1$–$C_4$)alkyl, phenyl- or nitrophenyl($C_1$–$C_4$)alkoxycarbonyloxy($C_1$–$C_4$)alkyl and the most preferable one may be 1-(t-butyldimethylsilyloxy)ethyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl and the most preferable one may be methyl.

Suitable "1-(lower)alkyl-1-hydroxy($C_2$–$C_6$)alkyl" may include 1-methyl-1-hydroxyethyl, 1-ethyl-1-hydroxyethyl, 1-propyl-1-hydroxypropyl, 1-butyl-1-hydroxybutyl, 1-isopropyl-1-hydroxy-2-methylpropyl, 1-methyl-1-hydroxypentyl, 1-ethyl-1-hydroxy-2-(or 3-)methylbutyl, 1-pentyl-1-hydroxy-2,2-dimethylpropyl, 1-hexyl-1-hydroxyhexyl, and the like, in which more preferable one may be 1-($C_1$–$C_4$)alkyl-1-hydroxy($C_2$–$C_4$)alkyl and the most preferable one may be 1-methyl-1-hydroxyethyl.

Suitable "1-(lower)alkyl-1-(protected hydroxy) ($C_2$–$C_6$)alkyl" means aforementioned 1-(lower)alkyl-1-hydroxy($C_2$–$C_6$)alkyl, in which the hydroxy group is protected by a conventional hydroxy-protective group as mentioned above, in which preferable example may be 1-($C_1$–$C_4$)alkyl-1-[tri($C_1$–$C_4$)alkylsilyloxy] ($C_2$–$C_4$)alkyl and 1-($C_1$–$C_4$)alkyl-1-[phenyl- or nitrophenyl($C_1$–$C_4$)alkoxycarbonyloxy] ($C_2$–$C_4$)alkyl, and the most preferable one may be 1-methyl-1-(trimethylsilyloxy)ethyl.

Suitable "acyl" may be the aforementioned acyl as exemplified for the imino-protective group, in which more preferable example may be $C_1$–$C_4$ alkanoyl and the most preferable one may be acetyl.

Suitable "protected carboxy" may include esterified carboxy such as lower alkoxycarbonyl (e.g. methoxycarbonyl, ethoxycarbonyl, propoxycarbonyl, isopropoxycarbonyl, butoxycarbonyl, tert-butoxycarbonyl, etc.), $C_2$–$C_6$ alkenyloxycarbonyl (e.g. vinyloxycarbonyl, allyloxycarbonyl, etc.), mono(or di or tri)phenyl(lower)alkoxycarbonyl which may have a nitro group (e.g. benzyloxycarbonyl, 4-nitrobenzyloxycarbonyl, phenethyloxycarbonyl, benzhydryloxycarbonyl, trityloxycarbonyl, etc.), and the like, in which more preferable example may be $C_2$–$C_4$ alkenyloxycarbonyl and phenyl- or nitrophenyl ($C_1$–$C_4$)alkoxycarbonyl, and the most preferable one may be allyloxycarbonyl and 4-nitrobenzyloxycarbonyl.

The processes for the preparation of the object compound (I) of the present invention are explained in detail in the following.

(1) Process 1

The compound (I) or salts thereof can be prepared by reacting the compound (II) or salts thereof with the compound (III) or salts thereof, in the presence of an enolizating agent.

Suitable salts of compounds (II) and (III) may be the same as those for the compound (I).

Suitable enolizating agent may include tin compound such as stannous (lower)alkylsulfonate which may have halogens such as stannous polyhalo (lower) alkylsulfonate, preferably stannous perhalo ($C_1$–$C_4$) alkylsulfonate (e.g. stannous trifluoromethanesulfonate, etc.), and the like.

The reaction may also be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds {e.g. pyridine, picoline, lutidine, N,N-di(lower)alkylaminopyridine such as N,N-dimethylaminopyridine, etc.}, quinoline, imidazole, N-lower alkylmorphorine (e.g. N-methylmorphorine, etc.), N-lower alkylpiperidine (e.g. N-ethylpiperidine, etc.), N,N-di(lower)alkylbenzylamine (e.g. N,N-dimethylbenzylamine, etc.), and the like.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

The reaction temperature of this reaction is not critical and the reaction is usually carried out under from cooling to warming.

This reaction can be carried out in the presence of zinc halide (e.g. zinc chloride, zinc bromide, zinc iodide, etc.).

(2) Process 2

The compound (I-b) or salts thereof can be prepared by subjecting the compound (I-a) or salts thereof to removal reaction of the hydroxy-protective group in $R_a^4$.

Suitable salts of the compounds (I-b) and (I-a) may be the same as those for the compound (I).

This removal reaction is carried out by a conventional method such as hydrolysis, reduction, and the like, which can be selected according to the kind of hydroxy-protective group to be removed.

(i) Hydrolysis:

Hydrolysis is preferably carried out in the presence of a base or an acid. Suitable base may include an alkali metal hydroxide (e.g. sodium hydroxide, potassium hydorxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkalimetal alkoxide (e.g. sodium methoxide, sodium ethoxide, potassium t-butoxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, oxalic acid, acetic acid, propionic acid, trifluoroacetic acid, benzenesulfonic acid, p-toluneslufonic acid, etc.) and an inorganic acid (e.g. hydrochloric acid, hydrobromic acid, sulfuric acid, phosphoric acid, etc.), what is called Lewis acid such as boron trihalide (e.g. boron trichloride, boron trifluoride, boron trifluoride etherate, etc.) The acidic hydrolysis using trifuoroacetic acid is usually accelerated by addition of cation trapping agent (e.g. phenol, anisole, etc.).

In case that the hydroxy-protective group is tri(lower)alkylsilyl, the hydrolysis can also be carried out in the presence of tetra(lower)alkylammonium halide (e.g. tetrabutylammonium fuloride, etc.).

This reaction is usually carried out in a conventional solvent which does not adversely influence the reaction such as water, alcohol (e.g. methaol, ethanol, etc.), tetrahydrofuran, dioxane, acetone, acetonitrile, etc., or a mixture thereof. A liquid base or acid can also be used as the solvent.

The reaction temperature is not critical and the reaction is usually carried out under from cooling to warming.

(ii) Reduction:

The reduction method applicable to this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.), and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

The reaction is usually carried out in a conventional solvent which does not adversely influence the reaction such as water, alcohol (e.g. methanol ethanol, propanol, etc.), dioxane, tetrahydrofuran, acetic acid, buffer solution (e.g. phosphate buffer, etc.), and the like, or a mixture thereof.

The reaction temperature is not critical and the reaction is usually carried out under from cooling to warming.

(3) Process 3

The compound (I-d) or salts thereof can be prepared by introducing the imino-protective group into the compound (I-c) or salts thereof.

Suitable salts of the compounds (I-d) and (I-c) may be the same as those for the compound (I).

Suitable introducing agent of the imino-protective group may be a conventional one which can introduce an imino-protective group such as acyl mentioned above, into the compound (I-c), in which more preferable example may be ($C_1$–$C_4$) alkyl oxalyl halide (e.g. ethyl oxalyl chloride, etc.).

This reaction can be carried out in the presence of a base such as that exemplified in the explanation of Process 1.

This reaction is usually carried out in a conventional solvent which does not adversely influence the reaction such as dichloromethane, chloroform, ethyl acetate, tetrahydrofuran, dioxane, acetone, etc., or a mixture thereof.

The reaction temperature is not critical and the reaction is usually carried out under from cooling to warming.

(4) Process 4

The compound (I-f) or salts thereof can be prepared by subjecting the compound (I-e) or salts thereof to removal reaction of the hydroxy-protective group in $R_a{}^2$.

Suitable salts of the compounds (I-f) and (I-e) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the hydroxy-protective group of the compound (I-a) in Process 2, and therefore are to be referred to said explanation.

The methods A to D for the production of the known key intermediates for the 1-(lower)alkylcarbapenem compounds are explained in detail in the following.

(A) Method A

The compound (A-1) or salts thereof can be prepared by reacting the compound (I-b) or salts thereof with an oxidizing agent.

Suitable salts of the compound (A-1) may be the same as those for the compound (I).

Suitable oxidizing agent may include a conventional one such as perhalogenic acid (e.g. periodic acid, etc.) or a salt thereof, which can oxidize α-hydroxyketone

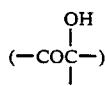

into carboxylic acid (—COOH).

Suitable salt of perhalogenic acid may be a salt with a base such as an inorganic base salt, for example, an alkali metal salt (e.g. sodium salt, potassium salt, lithium salt, etc.), and the like.

This reaction is usually carried out in a conventional solvent which does not adversely influence the reaction such as tetrahydrofuran, dioxane, water, alcohol (e.g. methanol, ethanol, etc.), buffer solution (e.g. phosphate buffer, acetate buffer, etc.), etc., or a mixture thereof.

The reaction temperature is not critical and the reaction is usually carried out under from cooling to warming.

(B) Method B

The compound (A-2) or salts thereof can be prepared by solvolysing the compound (I-e) or salts thereof.

Suitable salts of the compounds (A-2) and (I-e) may be the same as those for the compound (I).

The solvolysis may include hydrolysis, alcoholysis, and the like, and can be carried out in substantially the same manner as that of hydrolysis exemplified in the explanation of Process 2, and therefore, the reaction conditions (e.g. a base or an acid to be used, solvent, reaction temperature, etc.) are to be referred to the said explanation.

The alcoholysis is usually carried out in a conventional lower alcohol such as methanol, ethanol, propanol, and the like.

(C) Method C

The compound (A-4) or salts thereof can be prepared by subjecting the compound (A-3) or salts thereof to removal reaction of the imino-protective group.

Suitable salts of the compounds (A-4) and (A-3) may be the same as those for the compound (I).

This reaction is usually carried out by a conventional method such as solvolysis, reduction, and the like.

The method of solvolysis and reduction, and the reaction conditions (e.g. solvent, reaction temperature, etc.) are substantially the same as those illustrated for removal reaction of hydroxy-protective group of the compound (I-a) in Process 2 and the solvolysis of the compound (I-e) in Method B, and therefore are to be referred to the said explanation.

(D) Method D

The compound (A-5) or salts thereof can be prepared by reacting the compound (I-e) or salts thereof with compound (IV).

Suitable salts of the compound (A-5) may be the same as those for the compound (I).

This reaction can be carried out in the presence of an base as exemplified for the explanation of Process 1.

This reaction is usually carried out in a conventional solvent which does not adversely influence the reaction such as water, dichloromethane, acetonitrile, alcohol (e.g. methanol, ethanol etc.), tetrahydrofuran, dioxane, acetone, etc., or a mixture thereof.

The reaction temperature is not critical and the reaction is usually carried out under from cooling to heating.

The compounds (A-1), (A-2), (A-4) and (A-5) produced in the above Methods A to D can be transformed by known methods into antimicrobial 1-(lower)alkyl-carbapenem compounds.

The object compound (I), especially the optically active compound (I'), of the present invention is useful intermediates for the preparation of the above known key intermediates, and further the process of the present invention is also useful for the preparation of such optically active compound.

The following examples are given for the purpose of illustrating this invention in more detail.

EXAMPLE 1

To a suspension of stannous trifluoromethanesulfonate (8.35 g) and N-ethylpiperidine (3.79 ml) in dichloromethane (60 ml) was added dropwise a solution of 3-propionyl-2-thioxothiazolidine (4.12 g) in dichloromethane (35 ml) at −78° C. under nitrogen atmosphere. After stirring at −78° C. for 30 minutes, a solution of (3R,4R)-4-acetoxy-3-[(1R)-1-(t-butyldimethylsilyloxy)ethyl]-2-azetidinone (2.25 g) in dichloromethane (8 ml) was added to the reaction mixture, and the reaction mixture was stirred at 0° C. for 30 minutes and then at room temperature for 20 minutes. The reaction mixture was poured into aqueous sodium bicarbonate solution (100 ml) and the precipitated white mass was removed by passing through a layer of celite. The organic layer was separated and washed with 10% aqueous sodium chloride solution (100 ml×2). The organic solution was dried over magnesium sulfate and evaporated. The residue was chromatographed on silica gel (185 g) eluting with a mixture of acetone and dichloromethane (2:98, V/V) to give (3S,4R)-3-[(1R)-1-(t-butyldimethylsilyloxy)ethyl]-4-[(1RS)-1-methyl-2-oxo-2-(2-thioxothiazolidin-3-yl)ethyl]-2-azetidinone (2.39 g).

IR (CH$_2$Cl$_2$): 1760, 1690 cm$^{-1}$.

NMR (CDCl$_3$, δ): 0.07 (6H, s), 0.87 (9H, s), 1.17 (3H, d, J=4.5 Hz), 1.27 (3H, d, J=4.5 Hz), 2.77 (0.17H, dd, J=6.0, 3.0 Hz) 3.00 (0.83H, dd, J=4.5, 3.0 Hz), 3.26 (2H, t, J=6.5 Hz), 3.92 (1H, dd, J=4.5, 3.0 Hz), 4.16 (1H, dq, J=6.0, 4.5 Hz), 4.53 (2H, t, J=6.5 Hz), 4.93 (1H, dq, J=6.5, 4.5 Hz), 6.20 (1H, br s).

The above NMR data show the ratio of (1R)-1-methyl isomer to (1S)-1-methyl isomer is 4.9:1.

EXAMPLE 2

To a suspension of stannous trifluoromethanesulfonate (1.63 g) and N-ethylpiperidine (0.827 ml) in dichloromethane (12 ml) was added dropwise a solution of 3-propionyl-2-thioxothiazolidine (1.07 g) in dichloromethane (9 ml) at −78° C. under nitrogen atmosphere. After stirring at −78° C. for 30 minutes, a solution of (3R,4R)-4-acetoxy-3-[(1R)-1-(t-butyldimethylsilyloxy)ethyl]-2-azetidinone (0.876 g) and zinc bromide (1.37 g) in dichloromethane (3 ml) was added to the reaction mixture, and the reaction mixture was stirred at −20° C. for 15 hours. The reaction mixture was poured into aqueous sodium bicarbonate solution (30 ml) and the precipitated white mass was removed by passing through a layer of Celite. The organic layer was separated and washed with 10% aqueous sodium chloride solution (30 ml×2). The organic solution was dried over magnesium sulfate and evaporated. The residue was chromatographed on silica gel (21 g) eluting with a mixture of acetone and dichloromethane (2:98, V/V) to give (3S,4R)-3-[(1R)-1-(t-butyldimethylsilyloxy)ethyl]-4-[(1RS)-1-methyl-2-oxo-2-(2-thioxothiazolidin-3-yl)ethyl]-2-azetidinone (878 mg).

NMR (CDCl$_3$, δ): 0.07 (6H, s), 0.87 (9H, s), 1.17 (3H, d, J=4.5 Hz), 1.27 (3H, d, J=4.5 Hz), 2.77 (0.2H, dd, J=6.0, 3.0 Hz) 3.00 (0.8H, dd, J=4.5, 3.0 Hz), 3.26 (2H, t, J=6.5 Hz), 3.92 (1H, dd, J=4.5, 3.0 Hz), 4.16 (1H, dq, J=6.0, 4.5 Hz), 4.53 (2H, t, J=6.5 Hz), 4.93 (1H, dq, J=6.5, 4.5 Hz), 6.20 (1H, br s).

The above NMR data show the ratio of (1R)-1-methyl isomer to (1S)-1-methyl isomer is 4:1.

EXAMPLE 3

To a suspension of stannous trifluoromethanesulfonate (2.18 g) and N-ethylpiperidine (590 mg) in dichloromethane (15 ml) was added dropwise a solution of 2-methyl-2-(trimethylsilyloxy)-3-pentanone (785 mg) in dichloromethane (2 ml) at −78° C. under argon atmosphere. After stirring for 30 minutes, a solution of (3R,4R)-4-acetoxy-3-[(1R)-1-(t-butyldimethylsilyloxy)ethyl]-2-azetidinone (300 mg) in dichloromethane (3 ml) was added dropwise to the mixture. The reaction mixture was allowed to warm to room temperature and stirred at the same temperature for 3 hours. The mixture was quenched with phosphate butter (pH 7). The organic layer was filtered with celite, washed with dichloromethane, dried over magnesium sulfate and evaporated. The residue was chromatographed on silica gel (9 g) eluting with a mixture of ethyl acetate and hexane (1:10, V/V) to give (3S,4R)-3-[(1R)-1-(t-butyldimethylsilyloxy)ethyl]-4-[(1R)-1,3-dimethyl-3-(trimethylsilyloxy)-2-oxobutyl]-2-azetidinone (159 mg).

mp: 162° C.

IR (CDCl$_3$): 3420, 1755, 1710, 1250 cm$^{-1}$.

NMR (CDCl$_3$, δ): 0.00 (6H, s), 0.13 (9H, s), 0.80 (9H, s), 1.10 (3H, d, J=6.0 Hz), 1.15 (3H, d, J=6.0 Hz), 1.23 (3H, s), 1.28 (3H, s), 2.85 (1H, dd, J=6.0, 3.0 Hz), 2.97-3.20 (1H, m), 3.76 (1H, dd, J=6.0, 3.0 Hz), 4.13 (1H, dq, J=6.0, 6.0), 5.88 (1H, br s).

EXAMPLE 4

To a solution of (3S,4R)-3-[(1R)-1-(t-butyldimethylsilyloxy)ethyl]-4-[(1RS)-1-methyl-2-oxo-2-(2-thioxothiazolidin-3-yl)ethyl]-2-azetidinone obtained in Example 1 (594 mg) in acetonitrile (18 ml) were added magnesium salt of mono 4-nitrobenzyl ester of malonic acid (636 mg) and imidazole (130 mg), and the mixture was stirred at 60° C. for 2 hours under nitrogen atmosphere. The reaction mixture was evaporated and the residue was dissolved in ethyl acetate (10 ml). The solution was washed in turn with 0.5N hydrochloric acid (10 ml×2), 5% aqueous potassium carbonate (10 ml×2) and water (10 ml), and dried over magnesium sulfate and evaporated. The residue was chromatographed on silica gel (23 g) eluting with a mixture of hexane and ethyl acetate (3:2, V/V) to give 4-nitrobenzyl (4R)-4-[(2R,3S)-3-{(1R)-1-(t-butyldimethylsilyloxy)ethyl}-4-oxoazetidin-2-yl]-3-oxopentanoate (595 mg) containing a very small amount of (4S)-isomer.

IR (CH$_2$Cl$_2$): 1750 cm$^{-1}$.

NMR (CDCl$_3$, δ): 0.12 (6H, s), 0.92 (9H, s), 1.21 (3H, d, J=7.0 Hz), 1.23 (3H, d, J=7.5 Hz), 2.93 (1H, dd, J=5.0, 3.0 Hz), 2.6-3.1 (1H, m), 3.65 (2H, s), 3.95 (1H, dd, J=4.5, 3.0 Hz), 4.18 (1H, m), 5.27 (2H, s), 5.98 (1H, s), 7.48 (2H, d, J=8.4 Hz), 8.21 (2H, d, J=8.4 Hz).

EXAMPLE 5

To a solution of (3S,4R)-3-[(1R)-1-(t-butyldimethylsilyloxy)ethyl]-4-[(1RS)-1-methyl-2-oxo-2-(2-thioxothiazolidin-3-yl)ethyl]-2-azetidinone obtained in Example 2 (797 mg) in methanol (16 ml) was added potassium carbonate (410 mg) at 0° C. and the mixture was stirred at room temperature for 10 minutes. The reaction mixture was poured into a mixture of ethyl acetate (40 ml), saturated aqueous sodium chloride (25 ml) and 1N hydrochloric acid (3 ml). The organic layer was separated, washed with saturated aqueous sodium chloride solution (30 ml ×2), dried over magnesium sulfate and evaporated. The residue was chromatographed on silica gel (21 g) eluting with a mixture of hexane and ethyl acetate (3:2, V/V) to give methyl (2R)-2-[(2S,3S)-3-{(1R)-1-(t-butyldimethylsilyloxy)ethyl}-4-oxoazetidin-2-yl]propionate (597 mg) containing a very small amount of methyl (2S)-2-[(2S,3S)-3-{(1R)-1-(t-butyldimethylsilyloxy)ethyl}-4-oxoazetidin-2-yl]propionate.

IR (CH$_2$Cl$_2$): 1760, 1740 cm$^{-1}$

NMR (CDCl$_3$, δ): 0.07 (6H, s), 0.87 (9H, s), 1.15 (3H, d, J=7.0 Hz), 1.24 (3H, d, J=7.0 Hz), 2.4-2.9 (1H, m), 2.95 (1H, dd, J=2.5, 4.0 Hz), 3.66 (3H, s), 3.83 (1H, dd, J=2.5, 5.0 Hz), 4.0-4.4 (1H, m), 6.12 (1H, br s).

EXAMPLE 6

To a solution of (3S,4R)-3-[(1R)-1-(t-butyldimethylsilyloxy)ethyl]-4-[(1R)-1,3-dimethyl-3-(trimethylsilyloxy)-2-oxobutyl]-2-azetidinone (132 mg) in methanol (6 ml) was added oxalic acid dihydrate (200 mg) at room temperature and the mixture was stirred for 1 hour. The reaction mixture was evaporated, and diethyl ether (30 ml) and saturated aqueous sodium bicarbonate (10 ml) were slowly added to the residue. The solution was extracted twice with diethyl ether, and the extracts were combined and washed in turn with saturated aqueous sodium bicarbonate and brine. The organic layer was dried over magnesium sulfate and evaporated to give (3S,4R)-3-[(1R)-1-(t-butyldimethylsilyloxy)ethyl]-4-[(1R)-3-hydroxy-1,3-dimethyl-2-oxobutyl]-2-azetidinone (109 mg).

mp: 103° C.

IR (CDCl$_3$): 3800–3200, 3430, 1760, 1740 cm$^{-1}$.

NMR (CDCl$_3$, δ): 0.08 (6H, s), 0.89 (9H, s), 1.20 (3H, d, J=7.5 Hz), 1.26 (3H, d, J=6.0 Hz), 2.70 (1H, m), 3.00 (1H, dd, J=2.0, 4.5 Hz), 3.92 (1H, dd, J=2.0, 6.0 Hz), 4.18 (1H, m), 6.32 (1H, br s).

EXAMPLE 7

To a solution of (3S,4R)-3-[(1R)-1-(t-butyldimethylsilyloxy)ethyl]-4-[(1R)-3-hydroxy-1,3-dimethyl-2-oxobutyl]-2-azetidinone (135 mg) in tetrahydrofuran (4 ml) was added 1M solution of sodium periodate buffered with acetic acid (mole ratio 1:1) (7.8 ml) at room temperature and the mixture was stirred for 1 day at the same temperature. The reaction mixture was evaporated, acidified, and extracted twice with dichloromethane. The organic layer was washed twice with brine, dried over magnesium sulfate and evaporated to give (2R)-2-[(2S,3S)-3-{(1R)-1-(t-butyldimethylsilyloxy)ethyl}-4-oxoazetidin-2-yl]propionic acid (85 mg).

mp: 124° C. (dec.).

IR (CHCl$_3$): 3480, 3410, 1755, 1700 cm$^{-1}$.

NMR (CDCl$_3$, δ): 0.07 (6H, s), 0.87 (9H, s), 1.17 (6H, d, J=6.0 Hz), 1.40 (6H, s), 2.90 (1H, dd, J=3.3, 2.4 Hz), 3.32 (1H, dq, J=6.6, 7.2 Hz), 3.73 (1H, br s), 3.77 (1H, dd, J=7.5, 2.4 Hz), 4.08 (1H, dq, J=5.7, 7.5 Hz), 6.6 (1H, br s).

EXAMPLE 8

To a solution of (3S,4R)-3-[(1R)-1-(t-butyldimethylsilyloxy)ethyl]-4-[(1R)-1,3-dimethyl-3-(trimethylsilyloxy)-2-oxobutyl]-2-azetidinone (50 mg) in triethylamine (0.2 ml) and dichloromethane (1 ml) was added dropwise ethyl oxalyl chloride (26 μl) at 0° C. After stirring for 1 hour at room temperature, the reaction mixture was extracted with dichloromethane. The organic layer was washed with water, dried over magnesium sulfate and evaporated to give (3S,4R)-3-[(1R)-1-(t-butyldimethylsilyloxy)ethyl]-1-(ethoxalyl)-4-[(1R)-1,3-dimethyl-3-(trimethylsilyloxy)-2-oxobutyl]-2-azetidinone. To a solution of this product in methanol (2 ml) was added oxalic acid dihydrate (73 mg) at room temperature and the mixture was stirred for 1 hour. The reaction mixture was evaporated and extracted with ethyl acetate. The extract was washed in turn with brine and water, dried over magnesium sulfate and evaporated. The residue was chromatographed on silica gel (1 g) eluting with a mixture of ethyl acetate and hexane (1:2–1:3, V/V) to give (3S,4R)-3-[(1R)-1-(t-butyldimethylsilyloxy)ethyl]-1-(ethoxalyl)-4-[(1R)-3-hydroxy-1,3-dimethyl-2-oxobutyl]-2-azetidinone (76 mg).

EXAMPLE 9

To a solution of (3S,4R)-3-[(1R)-1-(t-butyldimethylsilyloxy)ethyl]-1-(ethoxalyl)-4-[(1R)-3-hydroxy-1,3-dimethyl-2-oxobutyl]-2-azetidinone (50 mg) in methanol (2 ml) was added 0.54M aqueous periodic acid solution (1.0 ml). After stirring at room temperature for 5 hours, the solvent was removed in vacuo and the residue was extracted with dichloromethane. The extract was dried over magnesium sulfate and evaporated to afford (2R)-2-[(2S,3S)-3-{(1R)-1-(t-butyldimethylsilyloxy)ethyl}-1-(ethoxalyl)-4-oxoazetidin-2-yl]propionic acid (93 mg). To a solution of the compound obtained above in diethyl ether (2 ml) was added a solution of diazomethane in diethyl ether at room temperature. The solvent was removed in vacuo and the residue was chromatographed on silica gel (1 g) eluting with a mixture of ethyl acetate and hexane (1:5, V/V) to give methyl (2R)-2-[(2S,3S)-3-{(1R)-1-(t-butyldimethylsilyloxy)ethyl}-1-(ethoxalyl)-4-oxoazetidin-2-yl]propionate (24 mg).

IR (CDCl$_3$): 1810, 1750, 1730, 1700 cm$^{-1}$.

NMR (CDCl$_3$, δ): −0.02 (3H, s), 0.02 (3H, s), 0.8 (9H, s), 1.16 (3H, d, J=6.0 Hz), 1.20 (3H, d, J=6.0 Hz), 1.30 (3H, t, J=7.5 Hz), 3.1–3.5 (2H, m), 3.67 (3H, s), 4.00–4.50 (2H, m), 4.33 (2H, q, J=7.5 Hz).

EXAMPLE 10

To a solution of methyl (2R)-2-[(2S,3S)-3-{(1R)-1-(t-butyldimethylsilyloxy)ethyl}-1-(ethoxalyl)-4-oxoazetidin-2-yl]propionate (27 mg) in methanol (1 ml) was added triethylamine (27 μl) at room temperature. After stirring for 30 minutes, the reaction mixture was extracted with ethyl acetate. The organic layer was washed with brine (twice) and water, dried over magnesium sulfate and evaporated to give methyl (2R)-2-[(2S,3S)-3-{(1R)-1-(t-butyldimethylsilyloxy)ethyl}-4-oxoazetidin-2-yl]propionate (14 mg).

IR (CH$_2$Cl$_2$): 1760, 1740 cm$^{-1}$.

EXAMPLE 11

To a suspension of stannous trifluoromethanesulfonate (1.48 g) and N-ethylpiperidine (404 mg) in dichloromethane (15 ml) was added dropwise a solution of 2-methyl-2-trimethylsilyloxy-3-pentanone (819 mg) in dichloromethane (5 ml) at −60°~70° C. under an argon atmosphere.

After the mixture was stirred for 1 hour, a solution of (3R,4R)-4-acetoxy-3-[(1R)-1-t-butyldimethylsilyloxyethyl]-2-azetidinone (500 mg) in dichloromethane (5 ml) was added dropwise to the mixture. The reaction mixture was allowed to warm to room temperature and stirred at the same temperature for 2 hours. The mixture was quenched with phosphate buffer (pH 7) and filtered with celite. The filtrate was washed twice with water, dried over magnesium sulfate and evaporated. The residue was chromatographed on silica gel eluting with a mixture of ethyl acetate and hexane (1:4–1:5, V/V) to give (3S,4R)-3-[(1R)-1-t-butyldimethylsilyloxyethyl]-4-[(1R)-1,3-dimethyl-3-trimethylsilyloxy-2-oxobutyl]-2-azetidinone (650 mg).

mp: 162° C.

IR (CHCl$_3$): 3420, 1755, 1710, 1250 cm$^{-1}$.

NMR (CDCl$_3$, δ): 0.00 (6H, s), 0.13 (9H, s), 0.8 (9H, s), 1.1 (3H, d, J=6.0 Hz), 1.15 (3H, d, J=6.0 Hz), 1.23 (3H, s), 1.28 (3H, s), 2.85 (1H, dd, J=6.0 and 3.0 Hz), 2.97–3.2 (1H, m), 3.76 (1H, dd, J=6.0 and 3.0 Hz), 4.13 (1H, dq, J=6.0 and 6.0 Hz), 5.88 (1H, br s).

[α]$_D^{17}$ −3.8° (c 1.0, CHCl$_3$).

EXAMPLE 12

To a stirred suspension of stannous chloride (37.9 g) in 1,2-dichloroethane (200 ml) was added trifluoromethanesulfonic acid (28.4 ml) and the mixture was heated at 80° C. under nitrogene atmosphere for 3 hours. To the reaction mixture was added 1,2-dichloroethane (200 ml) and heating was continued for another period of 7 hours. After cooling to −25° C., to the mixture were added successively N-ethylpiperidine (31.9 ml) and 3-propionyl-2-thioxothiazolidine (29.8 g) at −25° C.

After stirring at −20° C. for 2 hours, to the mixture was added a solution of (3R,4R)-4-acetoxy-3-[(1R)-1-(t-butyldimethylsilyloxy)ethyl]-2-azetidinone (28.7 g) in acetonitrile (100 ml), and the resultant mixture was allowed to warm to 0° C. and stirred at this temperature for 2 hours.

The reaction mixture was taken up into a mixture of disodium hydrogen phosphate 12-hydrate (10.5 g) and sodium dihydrogen phosphate dihydrate (2.9 g) in water (300 ml) and 1,2-dichloroethane (50 ml) at 5° C., and the resulting precipitate was removed by filtration through celite. The organic layer was separated, washed with brine (250 ml), dried over magnesium sulfate and evaporated. The residue was chromatographed on silica gel (170 ml) eluting with a mixture of dichloromethane and acetone (20:1–10:1 v/v) to give an oily residue which was taken up into diisopropyl ether (180 ml) and the mixture was stirred at ambient temperature for 1 hour. The resulting precipitate was removed by filtration and the filtrate was evaporated in vacuo to give an oily residue of (3S,4R)-3-[(1R)-1-(t-butyldimethylsilyloxy)-ethyl]-4-[(1R)-1-methyl-2-oxo-2-(2-thioxothiazolidin-3-yl)ethyl]-2-azetidinone and a small amount of (1S)-1-methyl isomer thereof, which was dissolved in acetonitrile (140 ml). To this solution was added boron trifluoride etherate (24.6 ml) at 5° C. and the mixture was stirred at ambient temperature for 8 hours.

The reaction mixture was taken up into a solution of sodium carbonate (18.3 g) in cold water (150 ml) and the mixture was stirred vigorously for 10 minutes, diluted with cold water (600 ml) and stirred at 0° C. for another period of 2 hours. The precipitate was collected by filtration, washed in turn with water (150 ml ×2) and diisopropyl ether (150 ml ×2), and dried in vacuo to give (3S,4R)-3-[(1R)-1-hydroxyethyl]-4-[(1R)-1-methyl-2-oxo-2-(2-thioxothiazolidin-3-yl)ethyl]-2-azetidinone (14.08 g).

IR (Nujol): 3450, 3180, 1740, 1710 cm$^{-1}$.

NMR (DMSO-d$_6$, δ): 1.06 (3H, d, J = 7 Hz), 1.15 (3H, d, J = 7 Hz), 2.81 (1H, dd, J = 2, 6 Hz), 3.1–3.5 (2H, m), 3.58 (1H, dd, J = 2, 7 Hz), 3.66–3.96 (1H, m), 4.2–4.63 (3H, m), 4.63–4.85 (1H, m), 8.06 (1H, br s).

EXAMPLE 13

To a stirred suspension of magnesium ethoxide (14.7 g) in tetrahydrofuran (250 ml) was added allyl hydrogen malonate (38.8 g) at 30° C. under nitrogen atmosphere. The resultant mixture was stirred at ambient temperature for 10 hours. To this mixture were added (3S,4R)-3-[(1R)-1-hydroxyethyl]-4-[(1R)-1-methyl-2-oxo-2-(2-thioxothiazolidin-3-yl)ethyl]-2-azetidinone (24.7 g) and imidazole (8.8 g), and the mixture was allowed to heat to 60° C. for 1 hour. After evaporation of the solvent in vacuo, the residue was taken up into a mixture of ethyl acetate (300 ml) and brine (200 ml). After adjusting to pH 3.5 with concentrated hydrochloric acid at 5° C., the organic layer was separated and diluted with brine (200 ml). After adjusting to pH 8 with 30% aqueous potassium carbonate at 5° C., the organic layer was separated, washed with brine, dried over magnesium sulfate and evaporated in vacuo. The residue was chromatographed on silica gel (600 ml) eluting with a mixture of dichloromethane and acetone (19:1–1:1 v/v) to give allyl (4R)-4-[(2R,3S)-3-{(1R)-1-hydroxyethyl}-4-oxoazetidin-2-yl]-3-oxopentanoate (19.46 g).

IR (CH$_2$Cl$_2$): 3680, 3600, 3510, 3410, 1760, 1710 cm$^{-1}$.

What we claim is:

1. A process for the preparation of 3,4-disubstituted-2-azetidinone compounds of the formula:

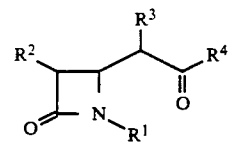

in which R$^1$ is hydrogen or amido-protective group, R$^2$ is hydroxy(lower)alkyl or protected hydroxy(lower)alkyl, R$^3$ is lower alkyl, and R$^4$ is 1-(lower)alkyl-1-hydroxy(C$_2$–C$_6$)alkyl, 1-(lower)alkyl-1-(protected hydroxy)-(C$_2$–C$_6$)alkyl or 2-thioxothiazolidin-3-yl, and salts thereof, which comprises reacting a compound of the formula:

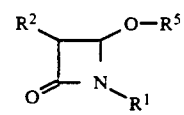

in which R$^1$ and R$^2$ are each as defined above, and or salts thereof, with a compound of the formula:

R$^3$—CH$_2$CO—R$^4$ in which R$^3$ and R$^4$ are each as defined above, or salts thereof, in the presence of an enolizating agent selected from the group consisting of stannous (lower)alkylsulfonate and stannous perhalo(lower)alkylsulfonate to give a compound of the formula:

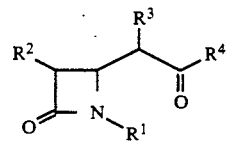

in which R$^1$, R$^2$, R$^3$ and R$^4$ are each as defined above, or salts thereof.

2. The process of claim 1, which the 3,4-disubstituted-2-azetidinone derivative is represented by the following configuration:

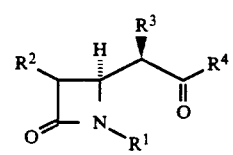

in which

R$^1$ is hydrogen, ar(lower)alkyl or acyl,

R$^2$ is hydroxy(lower)alkyl, acyloxy(lower)alkyl, ar(lower)alkoxy(lower)alkyl or trisubstituted silyloxy(lower)alkyl, and R$^4$ is 1-(lower)alkyl-1-hydroxy(C$_2$–C$_6$)alkyl, 1-(lower)alkyl-1-acyloxy(C$_2$–C$_6$)alkyl, 1-(lower)alkyl-1-[ar(lower)alkoxy]-(C$_2$–C$_6$)alkyl, 1-(lower)alkyl-1-(trisubstitutedsilyloxy) (C$_2$–C$_6$)alkyl, or 2-thioxothiazolidin-3-yl.

3. The process of claim 2, wherein $R^1$ is hydrogen, ar(lower)alkyl, phenyl- or nitrophenyl(lower)alkoxyoxalyl, or (lower)alkoxy-7-oxalyl, $R^2$ is hydroxy(lower)alkyl, tri(lower)alkylsilyloxy(lower)alkyl, or phenyl- or nitrophenyl(lower)alkoxycarbonyloxy(lower)alkyl, and $R^4$ is 1-(lower)alkyl-1-hydroxy $(C_2-C_6)$ alkyl, 1-(lower)alkyl-1-[tri(lower)alkylsilyloxy]$(C_2-C_6)$alkyl or 1-(lower)alkyl-1-[phenyl- or nitrophenyl(lower)alkoxycarbonyloxy]-$(C_2-C_6)$alkyl.

4. The process of claim 3, wherein $R^1$ is hydrogen or $(C_1-C_4)$alkoxyoxalyl, $R^2$ is hydroxy$(C_1-C_4)$alkyl or tri$(C_1-C_4)$alkylsilyloxy$(C_1-C_4)$alkyl, and $R^4$ is 1-$(C_1-C_4)$alkyl-1-hydroxy$(C_2-C_4)$alkyl or 1-$(C_1-C_4)$alkyl-1-[tri$(C_1-C_4)$alkylsilyloxy]$(C_2-C_4)$alkyl.

5. The process of claim 2, wherein $R^1$ is hydrogen, ar(lower)alkyl, pheny- or nitrophenyl(lower)alkoxyoxalyl, or (lower)alkoxyoxalyl, $R^2$ is hydroxy(lower)alkyl, tri(lower)alkylsilyloxy(lower)alkyl, or phenyl- or nitrophenyl(lower)alkoxycarbonyloxy(lower)alkyl, and $R^4$ is 2-thioxothiazolidin-3-yl.

6. The process of claim 5, wherein $R^1$ is hydrogen or $(C_1-C_4)$alkoxyoxalyl, and $R^2$ is hydroxy$(C_1-C_4)$alkyl or tri$(C_1-C_4)$alkyl.

7. The process of claim 6, wherein the 3,4-disubstituted-2-azotidinone derivative is [(3S,4R-3-[(1R)]-1-t-butyldimethylsilyloxyethyl)-4-[(1R)]-1-methyl-2-oxo-2-(2-thioxothiazolidin-3-yl)ethyl]-2-azetidinone, and the enolizing agent is stannous trifluoromethanesulfonate.

* * * * *